US005767328A

United States Patent [19]

Ono et al.

[11] Patent Number: 5,767,328
[45] Date of Patent: Jun. 16, 1998

[54] CYCLIC ALCOHOL AND PROCESS FOR PRODUCING THE SAME

[75] Inventors: Shigeru Ono; Mineyuki Iwasaki, both of Kurashiki, Japan

[73] Assignee: Asahi Kasei Kogyo Kabushiki Kaisha, Osaka, Japan

[21] Appl. No.: 770,051

[22] Filed: Dec. 19, 1996

[30] Foreign Application Priority Data

Dec. 21, 1995 [JP] Japan ..................... 7-333356

[51] Int. Cl.$^6$ ........................... C07C 29/20
[52] U.S. Cl. ........................... 568/835
[58] Field of Search ........................... 568/835, 822, 568/895, 832, 821, 838, 839

[56] References Cited

U.S. PATENT DOCUMENTS 5,302,762  4/1994  Yamashita et al.

FOREIGN PATENT DOCUMENTS 60-104028  7/1990  Japan .
5-221899  8/1993  Japan .

*Primary Examiner*—Gary Geist
*Assistant Examiner*—Karl J. Puttlitz, Jr.
*Attorney, Agent, or Firm*—Birch, Stewart, Kolasch & Birch, LLP

[57] ABSTRACT

A process for producing a cyclic alcohol which comprises subjecting a cyclic olefin represented by the formula: $C_nH_{2n-2-m}R_m$ (wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate having a primary particle diameter of 0.5 μm or less as a catalyst, extracting the resulting liquid of an oil phase containing a cyclic alcohol and the crystalline aluminosilicate, evaporating the liquid and feeding the vapor to a rectifying column and/or filtering the liquid and feeding the filtrate to the rectifying column, thereby to adjust the concentration of the crystalline aluminosilicate contained in the liquid in the rectifying column to 1000 ppm by weight or less, and subjecting the liquid to distillation to separate the cyclic alcohol.

14 Claims, No Drawings

CYCLIC ALCOHOL AND PROCESS FOR PRODUCING THE SAME

BACKGROUND OF THE INVENTION

1. Field of the Invention

The present invention relates to a process of carrying out catalytic hydration reaction of a cyclic alcohol in the presence of an oil phase containing the cyclic olefin, an aqueous phase and a crystalline aluminosilicate as a catalyst and separating the cyclic alcohol.

2. Description of the Related Art

Many literatures and patents disclose processes for producing cyclic alcohols by hydration reaction of cyclic olefins using crystalline aluminosilicates as solid catalysts.

JP-B-2-31056 proposes a process for producing a cyclic alcohol by hydrating a cyclic olefin using a crystalline aluminosilicate having a primary particle diameter of up to 0.5 μm as a catalyst. JP-B-2-31056 discloses that in the case of using a crystalline aluminosilicate having a primary particle diameter of up to 0.5 μm as a catalyst, when the weight ratio of the cyclic olefin to water is in the range of 0.001–100, two phases of an oil phase and an aqueous phase are formed in the reaction system and the crystalline aluminosilicate is present in the aqueous phase. Furthermore, it is disclosed that the cyclic alcohol produced by the reaction is mostly present in the oil phase and a mixture of the cyclic olefin and the cyclic alcohol obtained from the oil phase can be easily separated into the two components because they greatly differ in their boiling point, and, thus, the desired cyclic alcohol can be obtained. It mentions as a general example a process according to which a part of the reaction mixture comprising the two phases is continuously taken out and separated into layers in a still standing tank, and an oil phase is taken out from the upper layer and the cyclic alcohol is obtained from the oil phase by a means such as distillation or the like.

JP-B-2-31056 teaches that the crystalline aluminosilicate is not present in the oil phase, and, hence, it does not refer to the problems caused by the crystalline aluminosilicate in the oil phase.

JP-A-5-221899 proposes a process for producing a cycloalkanol by reacting a cycloolefin with water in the presence of a solid acid catalyst, characterized in that a mixture of water and the cycloolefin is led to a solid layer comprising the solid acid catalyst and allowed to pass through the layer and no observable liquid phase should be formed in the layer. It is mentioned that this process has an advantage that the reaction mixture is obtained being separated from the catalyst. Furthermore, it mentions, "The content in the reaction vessel had two liquid layers before, during and after the reaction. The catalyst was predominantly found in the lower (aqueous) phase.". However, it mentions neither the catalyst in the oil phase nor the effect exerted by the catalyst.

There are no literatures and patents which refer to problems or influences caused by the catalyst present in the oil phase.

However, the inventors have found that if the step of continuously separating into layers the reaction mixture comprising two phases in a still standing tank is industrially carried out in a large scale, a slight amount of the crystalline aluminosilicate inevitably incorporates into the oil phase. It has been further found that when cyclic alcohol is obtained by distilling the oil containing the crystalline aluminosilicate to separate the cyclic alcohol, the crystalline aluminosilicate in the oil phase is concentrated mainly into the cyclic alcohol during the distillation. There is a problem that the crystalline aluminosilicate present in the cyclic alcohol causes dehydration reaction of the once produced cyclic alcohol to produce a cyclic olefin and when the desired cyclic alcohol is separated and purified by distillation, incorporation of the cyclic olefin into the cyclic alcohol increases and cyclic alcohol of high purity can hardly be obtained. For example, if cyclohexene is contained in cyclohexanol, cyclohexene causes coloration in preparing adipic acid using the cyclohexanol as a starting material.

Moreover, the crystalline aluminosilicate concentrated into the cyclic alcohol deposits on the heat transfer surface of a reboiler used for distillation to result in deterioration of the heat transfer. If the heat transfer of the reboiler is deteriorated, separating performance in distillation lowers to increase incorporation of cyclic olefin into cyclic alcohol and this hinders a stable operation of long period of time.

SUMMARY OF THE INVENTION

The inventors have found that in obtaining a cyclic alcohol by distillation using a rectifying column, when the amount of crystalline aluminosilicate contained in the liquid in the rectifying column is up to 1000 ppm by weight, a cyclic alcohol of high purity which is low in cyclic olefin concentration can be obtained and, furthermore, a stable operation is possible without causing deterioration in heat transfer of reboiler in the rectifying column.

That is, the present invention relates to a cyclic alcohol of at most 500 ppm in cyclic olefin content which is obtained by subjecting a cyclic olefin represented by the formula:

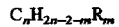

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate as a catalyst, subjecting the resulting oil to evaporation and/or filtration to remove the catalyst present in the oil, and, then, feeding the oil to a rectifying column, where the oil is distilled to separate the cyclic alcohol.

The present invention further relates to a process for producing a cyclic alcohol which comprises subjecting a cyclic olefin represented by the formula:

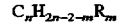

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate having a primary particle diameter of 0.5 μm or less as a catalyst, extracting the resulting liquid of an oil phase containing a cyclic alcohol and the crystalline aluminosilicate, evaporating the liquid and feeding the vapor to a rectifying column and/or filtering the liquid and feeding the filtrate to the rectifying column, thereby to adjust the concentration of the crystalline aluminosilicate contained in the liquid in the rectifying column to 1000 ppm by weight or less, and subjecting the liquid to distillation to separate the cyclic alcohol.

According to the process of the present invention, a cyclic alcohol of high purity which is low in cyclic olefin concentration can be obtained and it becomes possible to perform a stable operation without causing deterioration of heat transfer of the reboiler in the rectifying column used for the distillation and separation.

DESCRIPTION OF PREFERRED EMBODIMENTS

As examples of the crystalline aluminosilicate used in the present invention, mention may be made of mordenite, Faujasite, clinoptilolite, L-type zeolite, ZSM type zeolites developed by Mobil Chemical Co., chabazite, erionite, etc. Other effective examples are AZ-1 (JP-A-58-128210), TPZ-3 (JP-A-58-110419), Nu-3 (JP-A-57-3714), Nu-5 (JP-A-57-129820), Nu-6 (JP-A-57-123817), Nu-10 (JP-A-57-200218), etc. ZSM-5 is preferred.

The crystalline aluminosilicates in the present invention have a primary particle diameter of 0.5 µm or less, preferably 0.1 µm or less, more preferably 0.05 µm or less. The lower limit of the particle diameter is not critical as far as the aluminosilicates have "crystallinity", but the lower limit is preferably 0.01 µm. The crystal means a polyhedral solid formed by several definite plane surfaces exhibiting a certain symmetry owing to the regular and periodical arrangement of its atoms according to the symmetry, and the X-ray diffraction phenomenon is seen in the crystal ("Crystal" in Vol. 3, Page 349 of Kagaku Daijiten published from Kyoritsu Shuppan Co., Ltd. in 1963). Thus, in order that a certain periodicity exists and the X-ray diffraction phenomenon occurs, a certain finite size of crystal structure is present. Accordingly, it can be said that the crystalline aluminosilicate used in the present invention is one in which X-ray diffraction phenomenon is seen and which has a primary particle diameter of 0.5 µm or less. Hereupon, "the particle diameter being a certain size or less" means that particles of the size or less being 50% by weight of the total particles. If the particle diameter of primary particles is small, there is no problem even when secondary particles of larger diameter are formed due to agglomeration or the like.

In the present invention, the concentration of the crystalline aluminosilicate in the liquid in the rectifying column is 1000 ppm by weight or less, preferably 100 ppm by weight or less, more preferably 40 ppm by weight or less. The object of the present invention can be attained by adjusting the concentration to 1000 ppm by weight or less.

To adjust the concentration of the crystalline aluminosilicate in the liquid in the rectifying column to 1000 ppm by weight or less means that the concentration of the crystalline aluminosilicate is 1000 ppm by weight or less at any positions in the rectifying column. The position in the rectifying column where the concentration of the crystalline aluminosilicate becomes maximum depends on the rectifying conditions, but generally it is the area including the lower part and somewhat upper part from the cyclic alcohol extracting part (stage) and the part where the catalyst concentration increases by the distillation operation. In order to attain the catalyst concentration of 1000 ppm by weight or less in the liquid in the rectifying column, the catalyst concentration in the feed liquid must be controlled to from about one fifth or sixth to a several thousandth of the desired concentration.

Actually, it is difficult to carry out the control as one of operating conditions. Practically, the control is performed by using a device for removing the catalyst in the feed liquid or using a mist separator, or by evaporation of the catalyst, separation of the catalyst using a filter having controlled pore diameter, or the like.

The cyclic olefins in the present invention are those which are represented by the formula: $C_nH_{2n-2-m}R_m$ (wherein R represents a hydrogen atom, an alkyl group of 1–4 carbon atoms, a phenyl group or a cyclohexyl group, n represents an integer of 5–12, and m represents an integer of 1–4). Examples of the cyclic olefins are cyclopentene, methylcyclopentene, cyclohexene, methylcyclohexene, cyclooctene, cyclododecene, etc. Mixtures of these olefins are also useful. These cyclic olefins are hydrated to produce the corresponding cyclic alcohols.

The reaction temperature is preferably low from the viewpoints of chemical equilibrium of the hydration reaction of olefins and prevention of occurrence of side reactions, but if it is too low, undesirably, the reaction rate is small and a long time is required for the reaction. Thus, the reaction temperature is preferably 50°–300° C.

The reaction can be carried out under reduced pressure or under application of pressure. In the present invention, the pressure is preferably one under which both the cyclic olefin and water which are starting materials of the reaction can maintain liquid phases.

The molar ratio of the cyclic olefin and water which are starting materials can be employed in a wide range, but if the cyclic olefin is excessive, the conversion thereof decreases. If water is excessive, the capacity of the reaction vessel must be increased and the operation becomes difficult. Therefore, the weight ratio of water and the cyclic olefin is preferably 0.001–100.

The weight ratio of the cyclic olefin and the catalyst depends on reaction temperature, reaction pressure, molar ratio of the cyclic olefin and water, etc. in the case of carrying out the reaction continuously, and, in general, it is preferred that the weight of the catalyst is 0.01–200 times the weight of the cyclic olefin fed to the reaction vessel per 1 hour.

In the hydration reaction of cyclic olefins, side reactions such as isomerization and polymerization take place. For example, in the hydration reaction of cyclohexene, there are produced by-products such as methylcyclopentene, dicyclohexyl ether and bicyclohexyl. In order to prevent these side reactions and to obtain cyclic alcohols in high yields, it is effective to use, for example, crystalline aluminosilicate AZ-1 disclosed in Example 1 of JP-B-64-1453 as a catalyst.

The liquid subjected to distillation and separation in the present invention is the liquid of the oil phase produced by the above-mentioned catalytic hydration reaction and it contains a cyclic alcohol, a cyclic olefin and a slight amount of the crystalline aluminosilicate. In an ordinary operation, the concentration of the cyclic alcohol in this liquid is about 13% by weight. When the operation for separation of the catalyst is carried out industrially, it is preferred for downsizing apparatus to previously reduce the amount of the unreacted cyclic olefin and increase the concentration of the cyclic alcohol by distillation or the like. In this case, if the concentration of the cyclic alcohol is too high, the concentration of the coexisting crystalline aluminosilicate also increases and the dehydration reaction of the cyclic alcohol proceeds to cause loss in the yield. Therefore, the concentration of the cyclic alcohol in the liquid is preferably 15–99% by weight.

For removing the slight amount of the crystalline aluminosilicate catalyst from this liquid, it is effective to use an evaporator. As for the shape of the evaporator, a kettle type shell-and-tube cylindrical heat exchanger or the like is convenient and preferred. Specifically, the liquid is fed to the evaporator, where the oil containing mainly the cyclic olefin and cyclic alcohol is evaporated, and the vapor is fed to a rectifying column through a pipe or the like. On the other hand, the crystalline aluminosilicate remains in the evaporator mainly as an evaporation residue. This evaporation residue of crystalline aluminosilicate is intermittently or continuously drawn out of the system. Use of a pump or the like is convenient and preferred for drawing out the evaporation residue. When a pump is used, it is necessary not to lose the fluidity of the liquid drawn out, and, therefore, the concentration of the crystalline aluminosilicate is preferably lower than 50% by weight. Furthermore, in order to prevent the aluminosilicate from incorporating into vaporized oil in the form of splash, it is effective to provide a mist separator or the like midway of the pipe leading to the rectifying column.

Furthermore, for the removal of the crystalline aluminosilicate, filtration with a filter is also effective. The mean pore diameter of the filter is generally 0.1–5 μm, preferably 0.1–2 μm, more preferably 0.2–1 μm. Specifically, the liquid is fed to the filter and forced therethrough, and the filtrate lowered in the catalyst concentration is fed to the rectifying column through piping or the like. The crystalline aluminosilicate is captured mainly on the filter.

The filtration with a filter is more advantageous than the use of an evaporator in that the former is easier in operation because it does not need heat sources such as steam.

The filtering method includes the dead-end filtering method and the dynamic filtering method. ("Chemical Engineering", Vol.36, No.7, pages 34–35, published from Kagaku Kogyo Sha K.K.). The former dead-end filtering method is generally employed, but when this method is employed, the crystalline aluminosilicate captured on the filter forms a cake layer on the surface of the filter, which increases in its thickness with the lapse of time and causes decrease in the filtration amount of the liquid owing to increase of filtration resistance. Therefore, in order to obtain a stable filtration amount of liquid, for example, two or more of the similar filters are provided in parallel and with decrease of the filtration amount of the used equipment, this is replaced with spare equipment in succession and simultaneously the used filter is exchanged or cleaned.

On the other hand, the dynamic filtering method, for example, cross-flow filtering method is advantageous in that the cake layer on the filter surface is kept thin by shearing force of parallel flow and a stable filtration amount can be obtained for a long period of time.

The content of the crystalline aluminosilicate in the liquid of the oil phase containing a cyclic alcohol and a cyclic olefin in the following examples and comparative examples was obtained in the following manner: The liquid was filtered and the resulting filtration residue was washed, then, dried at 120° C. for 1 hour and further sintered at 500° C. for 4 hours, and the content was calculated from the weight of the resulting solid.

Moreover, fine particles of ZSM-5 described in JP-A-3-193622 were used as the crystalline aluminisilicate catalyst in the catalytic hydration reaction. The primary particle diameter of this crystalline aluminosilicate was 0.1 μm.

EXAMPLE 1

The above-mentioned crystalline aluminosilicate was mixed with water in an amount twice the weight of the aluminosilicate to prepare a slurry catalyst. The catalytic hydration reaction was carried out at a reaction temperature of 125° C. under a reaction pressure of 6 kg/cm$^2$G provided by pressurizing the vapor phase part with nitrogen gas, and at a revolution number of stirrer of 530 rpm by feeding 1 part by weight of cyclohexene per 1 hour for 1 part by weight of the catalyst. A disc-like diaphragm was provided in the upper part of the reaction vessel to vanish the dynamic pressure generated by stirring and mixing, and separation between oil and water under still standing was carried out in the upper part. The level of interface oil/water in the still standing part in the reaction vessel was positioned lower than the position of a nozzle for extracting the reaction product, and water in an amount corresponding to the amount of water consumed for the reaction was supplied through the starting material introducing pipe. The concentration of cyclohexanol and that of the crystalline aluminosilicate in the liquid of the oil phase produced in the reaction vessel were 11.8% by weight and 18 ppm by weight, respectively. Then, 100 parts by weight of the resulting liquid was fed to the third stage from the bottom of a sieve tray type rectifying column (No.1) having 22 practical plates, and 15.7 parts by weight of a cyclohexanol concentrate containing 25% by weight of cyclohexene and 113 ppm by weight of the crystalline aluminosilicate was obtained from the bottom. Composition of 84.3 parts by weight of the liquid distillate from the top of the column comprised nearly 100% of cyclohexene, both the cyclohexanol and the crystalline aluminosilicate being less than 1 ppm by weight.

The above cyclohexanol concentrate was fed to a kettle type evaporator and subjected to evaporation. The oil vapor was passed through a mist separator and, then, fed to a sieve tray type rectifying column (No.2), and the evaporation residue was extracted by a pump in an amount of 5% of the volume of the evaporator once a day. The rectifying column (No.2) was a sieve tray type rectifying column of 30 practical plates having a reboiler of steam heat source at the bottom. The oil vapor was fed to the 24th stage from the bottom, and the operation was carried out under a top pressure of 650 mmHg and at a reflux ratio of 3.4 with extracting from the bottom the liquid in an amount of 0.5% by weight based on the cyclohexanol concentrate, thereby to obtain cyclohexanol containing 2 ppm by weight of cyclohexene in an amount of 73.3% by weight based on the cyclohexanol concentrate from the sixth stage. In this case, the amount of the crystalline aluminosilicate at the bottom of the rectifying column (No.2) was 36 ppm by weight. After the operation for about 24 hours, the overall heat transfer coefficient of the reboiler showed no change, namely, it was 840 kcal/m$^2$/Hr/°C.

EXAMPLE 2

The cyclohexanol concentrate obtained in Example 1 which contained 25% by weight of cyclohexene and 113 ppm by weight of crystalline aluminosilicate was fed to a ceramic filter (having a pore diameter of 1 micron) of cross-flow filtration type to obtain a filtrate. The filtrate contained less than 1 ppm by weight of crystalline aluminosilicate. This filtrate was fed to the 24th stage from the bottom of a sieve tray type rectifying column (No.2) of 30 practical plates having a reboiler of steam heat source at the bottom, and the operation was carried out under a top pressure of 650 mmHg and at a reflux ratio of 0.132 with extracting from the bottom the liquid in an amount of 0.5% by weight based on the filtrate of the cyclohexanol concentrate, thereby to obtain cyclohexanol containing 2 ppm by weight of cyclohexene in an amount of 73.3% by weight based on the filtrate of the cyclohexanol concentrate from the sixth stage from the bottom. In this case, the amount of the crystalline aluminosilicate at the bottom of the rectifying column (No.2) was less than 1 ppm by weight. After the operation for about 24 hours, the overall heat transfer coefficient of the reboiler showed no change, namely, it was 840 kcal/m²/Hr/°C.

COMPARATIVE EXAMPLE 1

The cyclohexanol concentrate obtained in Example 1 which contained 25% by weight of cyclohexene and 113 ppm by weight of crystalline aluminosilicate was fed to the 24th stage from the bottom of a sieve tray type rectifying column (No.2) of 30 practical plates having a reboiler of steam heat source at the bottom, and the operation was carried out under a top pressure of 650 mmHg and at a reflux ratio of 0.132 with extracting from the bottom the liquid in an amount of 0.5% by weight based on the cyclohexanol concentrate, thereby to obtain cyclohexanol containing 1000 ppm by weight of cyclohexene in an amount of 73.3% by weight based on the cyclohexanol concentrate from the sixth stage from the bottom. In this case, the amount of the crystalline aluminosilicate at the bottom of the rectifying column (No.2) was 2.26% by weight. After the operation for about 24 hours, the overall heat transfer coefficient of the reboiler decreased to 810 kcal/m²/Hr/°C. from 840 kcal/m²/Hr/°C.

EXAMPLE 3

Example 2 was repeated, except that the crystalline aluminosilicate was added to the filtrate obtained in Example 2 to increase the crystalline aluminosilicate concentration to 4 ppm by weight. Cyclohexanol containing 40 ppm by weight of cyclohexene was obtained in an amount of 73.3% by weight based on the filtrate of the cyclohexanol concentrate from the sixth stage from the bottom. The amount of the crystalline aluminosilicate at the bottom of the rectifying column (No.2) was 800 ppm by weight. After the operation for about 24 hours, the overall heat transfer coefficient of the reboiler did not change, namely, it was 840 kcal/m²/Hr/°C.

This application is based on Japanese Patent Application No.7-333356 filed on Dec. 21, 1995 in Japan, the content of which is incorporated hereinto by reference.

What is claimed is:

1. A cyclic alcohol of at most 500 ppm in cyclic olefin content which is obtained by subjecting a cyclic olefin represented by the formula:

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate as a catalyst, subjecting the resulting oil to evaporation and/or filtration to remove the catalyst present in the oil, and, then, feeding the oil to a rectifying column to separate the cyclic alcohol by distillation.

2. A process for producing a cyclic alcohol which comprises subjecting a cyclic olefin represented by the formula:

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate having a primary particle diameter of 0.5 µm or less as a catalyst, extracting the resulting liquid of an oil phase containing a cyclic alcohol and the crystalline aluminosilicate, evaporating the liquid and feeding the vapor to a rectifying column and/or filtering the liquid and feeding the filtrate to the rectifying column, thereby to adjust the concentration of the crystalline aluminosilicate contained in the liquid in the rectifying column to 1000 ppm by weight or less, and subjecting the liquid to distillation to separate the cyclic alcohol.

3. A process according to claim 2, wherein the filtration of the liquid is carried out by dynamic filtration method.

4. A process according to claim 2, wherein the cyclic olefin is cyclohexene and the cyclic alcohol is cyclohexanol.

5. A process according to claim 2, wherein the catalytic hydration reaction is carried out at a reaction temperature of 50°–300° C.

6. A process according to claim 2, wherein the weight ratio of water and the cyclic olefin in the catalytic hydration reaction is 0.001–100.

7. A process according to claim 2, wherein the weight of the catalyst in the catalytic hydration reaction is 0.01–200 times the weight of the cyclic olefin fed per 1 hour.

8. A process according to claim 2, wherein when the liquid is evaporated and the resulting vapor is fed to the rectifying column, the vapor is passed through a mist separator provided midway of a pipe leading to the rectifying column.

9. A process according to claim 2, wherein when the liquid is filtered and the filtrate is fed to the rectifying column, the filter used for the filtration has a mean pore diameter of 0.1–5 µm.

10. A process for producing a cyclic alcohol which comprises subjecting a cyclic olefin represented by the formula:

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate having a primary particle diameter of 0.5 µm or less as a catalyst, extracting the resulting liquid of an oil phase containing a cyclic alcohol and the crystalline aluminosilicate, evaporating the liquid and feeding the vapor to a rectifying column and/or filtering the liquid and feeding the filtrate to the rectifying column, thereby to adjust the concentration of the crystalline aluminosilicate contained in the liquid in the rectifying column to 1000 ppm by weight or less, and subjecting the liquid to distillation to separate the cyclic alcohol; wherein when the liquid is evaporated and the resulting vapor is fed to the rectifying column, the evaporation residue is intermittently or continuously drawn out of the system.

11. A process for producing a cyclic alcohol which comprises subjecting a cyclic olefin represented by the formula:

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate having a primary particle diameter of 0.5 µm or less as a catalyst, extracting the resulting liquid of an oil phase containing a cyclic alcohol and the crystalline aluminosilicate, evaporating the liquid and feeding the vapor to a rectifying column and/or filtering the liquid and feeding the filtrate to the rectifying column, thereby to adjust the concentration of the crystalline aluminosilicate contained in the liquid in the rectifying column to 1000 ppm by weight or less, and subjecting the liquid to distillation to separate the cyclic alcohol; wherein when the liquid is evaporated and the resulting vapor is fed to the rectifying column, the liquid has been previously distilled before evaporation so that the concentration of the cyclic alcohol in the liquid is within the range of 15–99% by weight.

12. A process for producing a cyclic alcohol which comprises subjecting a cyclic olefin represented by the formula:

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate having a primary particle diameter of 0.5 μm or less as a catalyst, extracting the resulting liquid of an oil phase containing a cyclic alcohol and the crystalline aluminosilicate, evaporating the liquid and feeding the vapor to a rectifying column and/or filtering the liquid and feeding the filtrate to the rectifying column, thereby to adjust the concentration of the crystalline aluminosilicate contained in the liquid in the rectifying column to 1000 ppm by weight or less, and subjecting the liquid to distillation to separate the cyclic alcohol; wherein when the liquid is filtered and the filtrate is fed to the rectifying column, the liquid has been previously distilled before filtration so that the concentration of the cyclic alcohol in the liquid is within the range of 15–99% by weight.

13. A process for producing a cyclic alcohol which comprises subjecting a cyclic olefin represented by the formula:

$$C_nH_{2n-2-m}R_m$$

(wherein R represents a hydrogen atom, an alkyl group of 1–4 carbon atoms, a phenyl group or a cyclohexyl group, n represents an integer of 5–12, and m represents an integer of 1–4) to a catalytic hydration reaction with water in the presence of a crystalline aluminosilicate having a primary particle diameter of 0.5 μm or less as a catalyst, extracting the resulting liquid of an oil phase containing a cyclic alcohol and the crystalline aluminosilicate, evaporating the liquid and feeding the vapor to a rectifying column and/or filtering the liquid and feeding the filtrate to the rectifying column, thereby to adjust the concentration of the crystalline aluminosilicate contained in the liquid in the rectifying column to 1000 ppm by weight or less, and subjecting the liquid to distillation to separate the cyclic alcohol; wherein the crystalline aluminosilicate used as a catalyst has a primary particle diameter of 0.1 μm or less.

14. A process for reducing the content of a cyclic olefin in a cyclic alcohol which comprises evaporating a liquid containing a cyclic alcohol and suspected of containing a cyclic olefin and a crystalline aluminosilicate and feeding only the vapor to a rectifying column and/or filtering the liquid and feeding the filtrate to the rectifying column, thereby to reduce the concentration of the crystalline aluminosilicate contained in the liquid in the rectifying column to 1000 ppm by weight or less, and subjecting the liquid to distillation and separation.

* * * * *